United States Patent [19]
Abels et al.

[11] Patent Number: 5,466,447
[45] Date of Patent: Nov. 14, 1995

[54] METHOD FOR TREATING PSORIASIS

[75] Inventors: Robert I. Abels, Westfield; Karen Reilly, Cranford, both of N.J.

[73] Assignee: Amgen Inc., Thousand Oaks, Calif.

[21] Appl. No.: 230,662

[22] Filed: Apr. 21, 1994

Related U.S. Application Data

[63] Continuation of Ser. No. 762,667, Sep. 18, 1991, abandoned, which is a continuation of Ser. No. 213,194, Jun. 29, 1988, abandoned.

[51] Int. Cl.$^6$ .................................................. A61K 45/05
[52] U.S. Cl. ............................................................ 424/85.2
[58] Field of Search ............................................. 424/85.2

[56] References Cited

PUBLICATIONS

Ellis et al JAMA, vol. 256, (1986) pp. 3110–3116.
Donohue et al., *J. Immunol.*, 130(5) 1983, pp. 2203–2208.
Lee et al., *Arch. Dermatol.*, 124(12) 1988, pp. 1811–1815.
Aiba et al., *Arch Dermatol.*, Res. 1989, 281, pp. 310–315.
Zheny et al., *Int. J. Immunopharmacel.*, 1987, 9(5), pp. 539–549.
Kupper et al., PNAS, 1986, 83(12), pp. 4451–4455.
Kozin et al., *Vestm. Dermatol.*; Veneral 7, 1989, pp. 61–64.
Smith et al., *J. Rheumatol.*, 1989, 16(7), pp. 897–903.
Gottlieb, J. Am. Acad. Dermatol., 18, 1988, pp. 1376–1980.
Gaspari et al., JAMA, 1987, 258(12), pp. 1624–1629.
Ramseur et al., Cancer, 63, 1989, pp. 2005–2007.

*Primary Examiner*—Michael G. Wityshyn
*Assistant Examiner*—C. Sayala
*Attorney, Agent, or Firm*—Richard J. Mazza

[57] ABSTRACT

The present invention provides a therapeutic method of treating a human subject for psoriasis which comprises administering to the subject an effective psoriatic dermatosis-inhibiting amount of IL-2 and a pharmaceutically acceptable carrier.

16 Claims, No Drawings

METHOD FOR TREATING PSORIASIS

This application is a continuation of application Ser. No. 07/762,667 filed on Sep. 18, 1991, which in turn is a continuation of application Ser. No. 07/213,194 filed on Jun. 29, 1988, both now abandoned and both of which are hereby incorporated by reference.

BACKGROUND OF THE INVENTION

Psoriasis is a common chronic and recurrent disease characterized by hyperproliferation of the basal layer of the epidermis resulting in dry, well-circumscribed, silvery-scaled maculopapules and plaques of various sizes. The lesions occur predominently on the elbows, knees, scalp, and trunk and microscopically show characteristic parakeratosis and elongation of rete ridges. General health is rarely affected, although psoriatic arthritis, a destructive form of arthritis in the fingers and toes which often closely resembles rheumatoid arthritis, may develop in some patients.

Onset of psoriasis is usually gradual, however factors precipitating psoriatic eruptions include local trauma and occasionally severe sunburn, irritation, topical medications, chloroquine antimalarial therapy and withdrawal of systemic corticosteroids.

Although the cause of psoriasis is unknown, the following evidence implies that abnormalities in the cellular immune function exist:

1. depressed reactivity to contact allergen;
2. decreased delayed reactivity to interdermal challenge with antigen;
3. depressed response to major histocompatibility antigens;
4. depressed response to mitogens;
5. depressed lymphokine production to antigen challenge;
6. normal and decreased numbers of T-lymphocytes; and
7. decreased to normal suppressor T-lymphocyte function.

No current therapeutic methods exist which assure a cure for psoriasis. The simplest forms of treatment include topical applications of lubricants, keratolytics, and topical corticosteroids. Furthermore, a new treatment utilizing psoralens and high intensity ultraviolet A (PUVA) involves the oral administration of methoxsalen (average dose 40 mg) followed by exposure of the skin to long-wave ultraviolet light (330 to 360 nm). Although this treatment may produce remissions for several months, repeated treatments with intensive light may cause skin cancer. Finally the most effective treatment in severe disabling psoriasis that is unresponsive to topical agents or PUVA involves oral administration of methotrexate.

Interleukin-2 (IL-2) is a lymphokine, produced predominantly by helper T-cells, which modulates the activation and proliferation of cytotoxic T-cells, natural killer (NK) cells, B cells, lymphokine-activated killer (LAK) cells, and possibly T suppressor cells. Human IL-2 has been purified and its molecular structure has been determined. It is composed of a single polypeptide chain of 133 amino acid residues with a molecular weight of approximately 15,000 daltons which may be variably glycosylated without loss of biological activity. IL-2 and analogs thereof have been produced using recombinant DNA technology. For example, recombinant methionyl human interleukin-2 alanine-125 [r-met Hu IL-2 (ala-125)] is a non-glycosylated analog of natural human IL-2 which retains the full biological activity of recombinant natural sequence human IL-2 and is stable in vitro for at least six months. R-met Hu IL-2 (ala-125) differs from naturally-occurring human IL-2 by having an additional methionyl residue at position 1 and having the cysteine at position 125 substituted with an alanine residue. Its amino acid sequence, as well as methods for its production and purification, are disclosed in European patent publication number 136,489.

In clinical studies of recombinant IL-2 performed to date, toxicity has been dose related and has consisted mainly of fever, chills, rigors, malaise, diarrhea, fluid retention, nausea, vomiting, and arthralgias. Additionally, increased serum creatinine and transaminases, anemia, eosinophilia, leukocytosis, rash, stomatitis, hypotension, joint pain, and mental confusion have been reported.

Gaspari, et al., JAMA, 258: 1624–1629 (1987) reported the cutaneous effects which occurred in ten patients undergoing immunotherapy with IL-2 and autologous lymphokine-activated killer (LAK) cells, i.e., a subset of lymphoid cells activated with IL-2 which can mediate the regression of pulmonary and hepatic metastases originating from a variety of tumor cell lines, to treat cancer. Among their observations, Gaspari, et al. reported that pharmacologic doses of IL-2 exacerbated erythrodermic flare of psoriasis in two patients who presented with psoriasis.

One object of the present invention is to provide therapeutic methods of treating a subject for psoriasis.

SUMMARY OF THE INVENTION

The present invention provides a therapeutic method of treating a human subject for psoriasis. This method comprises administering to the subject an effective psoriatic dermatosis-inhibiting amount of IL-2 and a pharmaceutically acceptable carrier.

DETAILED DESCRIPTION OF THE INVENTION

Provided herein are therapeutic methods of treating a human subject for psoriasis. The therapeutic methods provided herein comprise administering to the subject an effective psoriatic dermatosis-inhibiting amount of IL-2 and a pharmaceutically acceptable carrier. Within this application "psoriatic dermatosis inhibiting" means inducing complete or partial regression or preventing recurrence of psoriasis. Additionally, within this application "interleukin-2" and "IL-2" each means a polypeptide with an amino acid sequence, at least a portion of which is present in the amino acid sequence of naturally-occurring human IL-2, said polypeptide being capable of modulating the activation and proliferation of human lymphocytes. Examples of such polypeptides are naturally-occurring human IL-2 and recombinant IL-2s such as the IL-2s disclosed in U.S. Pat. No. 4,738,927, the muteins disclosed in U.S. Pat. Nos. 4,518,584, 4,530,787 and 4,569,790, e.g., r IL-2$_{ser\ 125}$, the contents of each of which are incorporated by reference, and r-met Hu IL-2 (ala-125). In a preferred embodiment of the invention, the IL-2 is r-met Hu IL-2 (ala-125) or r IL-2$_{ser\ 125}$.

In one embodiment of the invention the IL-2 is administered to the subject parenterally, e.g., intravenously, intradermally, intramuscularly or subcutaneously, in which case the pharmaceutically acceptable carrier preferably comprises an isotonic buffer, e.g., a sodium acetate/glucose buffer. The intravenous administration of the IL-2 may be by infusion or preferably by bolus injection.

Generally, the dosage of IL-2 administration will vary depending on considerations such as age, general health, sex, degree of psoriatic eruptions and/or lesions, contraindications, if any, and other variables. Dosage may vary from at least 1,000 units IL-2/kilogram of body weight to about 40,000 units IL-2/kilogram of body weight, preferably about 10,000 units/kilogram to about 20,000 units/kilogram of body weight. Units (U) of IL-2 activity of a sample are determined by the following bioassay: CTLL cells are plated in wells of plastic tissue culture dishes in the absence of IL-2. At time =0, IL-2 samples (serially diluted) or IL-2 standards are added to the wells. After twenty hours incubation, tritiated thymidine is added and the cultures incubated for an additional four hours. Cells are then harvested, washed, disrupted, and their DNA collected on filters which are transferred to scintillation vials for radioactivity determination. The amount of radioactive thymidine incorporated into cellular DNA is proportional to the amount of IL-2 present in the sample. Units of activity of a sample are determined by comparing the dilution at which 50% maximal thymidine incorporation occurs with the dilution of standard causing 50% maximal thymidine incorporation.

Therapeutic regimens sufficient to effect complete or partial regression or prevent recurrence of psoriasis will also vary depending on such considerations as mentioned above regarding IL-2 dosage, and will be readily ascertainable by those skilled in the art without undue experimentation. Depending on such considerations, the IL-2 may be administered daily, e.g. o.d., b.i.d. or t.i.d., or continuously, e.g., by intravenous infusion or via a transdermal patch. Preferably the IL-2 is administered to the subject for at least two days. In one embodiment of the invention the IL-2 is administered for about four days. In another embodiment of the invention the IL-2 is administered for about ten days.

The following examples are provided by way of illustration and in no way limit the scope of the subject invention, which is defined by the claims appended hereto.

Example 1

Materials and Clinical Protocol

The final dosage form of r-met-Hu IL-2 (ala-125) for I.V. bolus injection included the following ingredients and their amounts diluted in either 1.1 ml or 5.3 ml H$_2$O:

| r-met-Hu-IL-2 (ala-125) | 0.45 ± 0.30 mg/ml |
|---|---|
| sodium acetate (buffer component) | 10 ± 5 mM |
| glucose | 4.9 ± 0.7% |

Patient 001, who presented with psoriatic dermatosis, received I.V. bolus injections of either of the above-mentioned dosage forms of r-met-Hu IL-2 (ala-125) as follows:

Day 1—10,000 U/kg
Day 2—20,000 U/kg
Day 3—20,000 U/kg
Day 4—Dose withheld
Day 5—10,000 U/kg On Day 8 the patient presented with exfoliative dermatitis and concurrent chills, fever, edema, total body rash and decreased range of motion in the extremities. r-met-Hu IL-2 (ala-125) therapy was discontinued until the patient recovered from the side effects. r-met-Hu IL-2 (ala-125) therapy was restarted on Day 15 and continued for five consecutive days at a dose of 2,500 U/kg.

Results

On Day 9 the patient began to show recovery from the exfoliative dermatitis as well as the psoriatic dermatosis. By the time r-met-Hu-IL-2 (ala-125) therapy was restarted on Day 15, the patient presented with neither the side effects of therapy nor psoriatic dermatosis. Additionally, the patient's psoriatic condition did not recur for approximately one month after therapy was initiated. Approximately one month after therapy was initiated the patient presented with a minor relapse of psoriatic dermatitis.

What is claimed is:

1. A therapeutic method of treating a human subject for a pre-existing condition of psoriasis, comprising administering to the subject having such pre-existing condition a daily dose of a pharmaceutical composition comprising (1) an amount of interleukin-2 from at least 1,000 units to about 40,000 units per kilogram of body weight sufficient to cause at least partial regression of such condition and (2) a pharmaceutically acceptable carrier.

2. A method according to claim 1, wherein the interleukin-2 is administered parenterally.

3. A method according to claim 2 wherein the pharmaceutically acceptable carrier comprises an isotonic buffer.

4. A method according to claim 2, wherein the interleukin-2 is administered intravenously.

5. A method according to claim 4, wherein the interleukin-2 is administered by bolus injection.

6. A method according to claim 4, wherein the interleukin-2 is administered by infusion.

7. A method according to claim 1, wherein the interleukin-2 comprises recombinant methionyl human interleukin-2 alanine-125.

8. A method according to claim 1, wherein the interleukin-2 comprises recombinant human interleukin-2 serine-125.

9. A method according to claim 1, wherein the composition is administered to the subject according to a therapeutic regimen sufficient to effect complete or partial regression or prevent recurrence of psoriasis.

10. A method according to claim 9, wherein the therapeutic regimen comprises administration of the interleukin-2 substantially daily.

11. A method according to claim 9, wherein about 10,000 units of interleukin-2 are administered to the subject per kilogram of the subject's body weight.

12. A method according to claim 9, wherein about 20,000 units of interleukin-2 are administered to the subject per kilogram of the subject's body weight.

13. A method according to claim 9, wherein the interleukin-2 is administered for at least two days.

14. A method according to claim 13, wherein the interleukin-2 is administered for about four days.

15. A method according to claim 13, wherein the interleukin-2 is administered for about ten days.

16. A therapeutic method of treating a human subject for a pre-existing condition of psoriasis which comprises administering to the subject by intravenous bolus injection a daily dose of a pharmaceutical composition comprising an amount of recombinant methionyl human interleukin-2 alanine 125 or recombinant human interleukin-2 serine 125 from at least 1000 to 40,000 units per kilogram of body weight and a pharmaceutically acceptable carrier.

* * * * *